(12) United States Patent
Farber

(10) Patent No.: US 10,500,190 B1
(45) Date of Patent: Dec. 10, 2019

(54) SUBLINGUAL OR BUCCAL ADMINISTRATION OF MELATONIN AND/OR VALERIAN

(71) Applicant: Michael Farber, Livingston, NJ (US)

(72) Inventor: Michael Farber, Livingston, NJ (US)

( * ) Notice: Subject to any disclaimer, the term of this patent is extended or adjusted under 35 U.S.C. 154(b) by 0 days.

(21) Appl. No.: 16/389,005

(22) Filed: Apr. 19, 2019

(51) Int. Cl.
| | |
|---|---|
| *A61K 31/4045* | (2006.01) |
| *A61K 47/22* | (2006.01) |
| *A61K 9/127* | (2006.01) |
| *A61P 25/20* | (2006.01) |
| *A61K 9/00* | (2006.01) |
| *A61K 36/84* | (2006.01) |
| *A61K 9/68* | (2006.01) |
| *A61K 9/20* | (2006.01) |
| *A61K 9/14* | (2006.01) |

(52) U.S. Cl.
CPC .......... *A61K 31/4045* (2013.01); *A61K 9/006* (2013.01); *A61K 9/1271* (2013.01); *A61K 36/84* (2013.01); *A61K 47/22* (2013.01); *A61P 25/20* (2018.01); *A61K 9/0058* (2013.01); *A61K 9/14* (2013.01); *A61K 9/2059* (2013.01)

(58) Field of Classification Search
None
See application file for complete search history.

(56) References Cited

U.S. PATENT DOCUMENTS

2016/0166543 A1* 6/2016 Joshi .................. A61K 31/4045
514/357

FOREIGN PATENT DOCUMENTS

WO   WO 2015/097611 A1 * 7/2015 ........... A61K 36/481

OTHER PUBLICATIONS

Si Oi et al., China Journal of Chinese Materia Medica (2013), 38(14), pp. 2309-2313.*
Si Qi et al., CAS SciFinder English language abstract (Database: Medline, Acc. No. 2014138632) of China Journal of Chinese Materia Medica (2013), 38(14), pp. 2309-2313.*

* cited by examiner

*Primary Examiner* — Brian J Davis
(74) *Attorney, Agent, or Firm* — Michael J. Feigin, Esq.; Feigin and Fridman LLC

(57) ABSTRACT

A pharmaceutical composition for sublingual or buccal administration of melatonin and valerian is complexed with a beta cyclodextrin or another complexation agent. It is then encased in a liposome. The molecules encased in the liposome are then dehydrated and compounded into any of a number of dosage forms such as a dissolvable strip of material, a gum, lozenge, mint, tablet, or powder.

12 Claims, No Drawings

SUBLINGUAL OR BUCCAL ADMINISTRATION OF MELATONIN AND/OR VALERIAN

FIELD OF THE DISCLOSED TECHNOLOGY

The disclosed technology relates to a particular compound and method of delivery thereof sublingually or bucally, and more specifically, to the delivery of melatonin and/or valerian.

BACKGROUND OF THE DISCLOSED TECHNOLOGY

Hormones such as the indole hormone, melatonin, are widely found in both the plant and animal kingdoms. Melatonin can be found in human milk, bananas, beets, cucumbers, and tomatoes. Chemically, melatonin is N-acetyl-5-methoxytrypta mine, a derivative of serotonin, which in turn is derived from tryptophan. Melatonin is a ubiquitous natural neurotransmitter-like compound produced primarily by the pineal gland and is involved in numerous aspects of the biological and physiologic regulation of body functions. See, e.g., Malhotra, S., et al., Medscape General Medicine 2004; 6(2), 46; and www.nlm.nih.gov/medlineplus/print/druginfo/natural/patient-melatonin.html for a further background discussion.

The role of endogenous melatonin in circadian rhythm disturbances and sleep disorders is well established. Some studies have shown that melatonin may also be effective in breast cancer, fibrocystic breast diseases, and colon cancer. Melatonin has been shown to modify immunity, the stress response, and certain aspects of the aging process; some studies have demonstrated improvements in sleep disturbances and in instances of jet lag disturbances. The antioxidant role of melatonin may be of potential use for conditions in which oxidative stress is involved in the pathophysiologic processes. The multiplicity of actions and variety of biological effects of melatonin suggest the potential for a range of clinical and wellness-enhancing uses, especially considering that as one ages, the production of this key hormone goes into steady decline. Indeed, for an octogenarian, the amount produced is quite nominal.

Through melatonin release, the pineal gland maintains the internal clock governing the natural rhythms of body function. This apparent clock-setting property of melatonin has led to the suggestion that it is a "chronobiotic" substance that alters and potentially normalizes biological rhythms and adjusts the timing of other critical processes and biomolecules (hormones, neurotransmitters, etc.) that, in turn, exert numerous peripheral actions. The sleep-inducing effects of melatonin have advantages over conventional hypnotics, since melatonin, itself, is not a hypnotic drug. Melatonin only induces a natural state of sleepiness, and does not have the adverse side-effects of conventional hypnotics and prescription sleeping aids.

Melatonin has previously been used pharmaceutically, and has been prepared for oral administration (see, e.g., WO 1995/003043). These preparations include melatonin formulated with a cyclodextrin (WO 1999/047175), and as a microemulsion (U.S. Pat. No. 5,362,745). However, as with most oral preparations, it can take more than 30 minutes, even upwards of over an hour, after administration for the blood plasma concentration of melatonin to reach its peak. Goldberg, M J, Bergstrom, R F R, Smith, B P, Simcox, E A, Thomasson, H R, Shipley, L A: Sleep Research 1997: 26:101. This is due, in part, to the need for gastrointestinal absorption to occur before the melatonin is available in the bloodstream.

Further, melatonin has low oral bioavailability. The proportion of the drug, when taken orally, which is available to the user is both poor and erratic. Melatonin's absolute oral bioavailability has been shown to be approximately from approximately 15% in some studies to as low as 2.5% in others and peak plasma concentrations can vary over 20 fold range. DeMuro R L, Nafziger A N, Blask D E, Menhinick A M, Bertino J S: Journal of Clinical Pharmacology 2000: 40; 781; Di W L, Kadva A, Johnston A, Silman R: New England Journal of Medcine 1997: 336; vol. 14, 1028. Thus, oral administration of melatonin in currently available preparations does not provide for rapid onset of action, and its poor and erratic GI absorption make it an unsuitable route of administration.

Several sublingual, buccal, orally dissolving tablets and films containing melatonin are also available commercially. For example, transmucosal formulations are described in WO 1996/030013 and U.S. Pat. No. 5,688,520. However, in these formulations, melatonin is compounded in its undissolved, or solid, state. For any drug to be absorbed into the bloodstream, it must be dissolved, i.e., in solution. Due to melatonin's poor water solubility much of the dosage from any currently available preparation is swallowed undissolved in the saliva, leading to poor and erratic absorption in the GI tract. Accordingly, hormone drugs such as melatonin having low to poor water solubility, are expected to be poorly suited for buccal or sublingual administration.

Other routes of administration for melatonin, including nasal and oral sprays have been considered. U.S. Pat. No. 6,007,834. However, sprays are less desirable because of inherent compliance issues such as improper manipulation of the actuator, swallowing of the dosage before dissolution of the drug, and the restrictions on usage when the patient has sinus congestion or a head cold. Again poor solubilization of the dosage will lead to poor absorption. This again leads to erratic and poor melatonin bioavailability. Therefore sprays are not the optimal route for routine melatonin administration.

Moving on to Valerian, valerian root extract has long been used as a herbal remedy for the treatment of sleep disorders. It has been postulated that the mechanism of action related to valerian extract is related to the soporific action of the valeprotiates and the GABA minergic action of valerenic acid. Thus the increased absorption of these essential compounds and their increased bioavailability through the complexation in the present invention allows for both faster absorption at the buccal mucosa and enhanced absorption at the small intestinal layer providing both rapid and prolonged effect within the same dosage form.

Research into the use of Valerian root extracts to treat symptoms of insomnia has shown extremely high variability of absorption both inter individual and intra individual and has therefore not met commercial success to date. That this high variability of effect and absorption is probably due to high variability of metabolism by the liver.

Accordingly, there is a need in the arts to provide rapid and consistent delivery of a sleep inducing hormone having low to poor water solubility, such as melatonin and valerian extract.

SUMMARY OF THE DISCLOSED TECHNOLOGY

The subject melatonin and valerian formulation can advantageously be useful to administer to a patient in significantly less time and with more consistent and higher bioavailability than previously available dosage forms. Therefore, this invention as claimed, provides a unique composition, delivery system and method of administration for a melatonin and valerian composition along with other hormones or effective molecules having low to poor water solubility.

Melatonin is poorly soluble in water or other aqueous biological fluids and, when delivered in a undissolved state, as in the currently available melatonin products, the drug remains undissolved in saliva and must therefore be swallowed in order to be absorbed in any substantial amount. Thus, for these products, the onset of action, absorption and first pass metabolism are no different than from swallowing an immediate-release oral tablet or capsule containing undissolved melatonin. Such tablets are considered to be immediate-release only due to the rapid disintegration of the dosage form. These available tablets or strips release melatonin in an undissolved state, and drug absorption is limited by the drug dissolving ineffectively in the local delivery area.

Unlike other sublingual tablets and orally disintegrating tablets or strips, where melatonin must first dissolve into the saliva to be absorbed, the subject invention advantageously provides the actives, both melatonin and valerian extract in a complexed form having high aqueous solubility. In the subject invention, the hormone such as melatonin is not provided as an emulsion or solid dispersion, but is completely complexed with both a cyclodextrin and liposomal complex having immediate absorption capabilities. Therefore melatonin sublingual/buccal delivery is enhanced by this invention, because melatonin/valerian complex rapidly and fully dissolves in the saliva. Further, by being formulated into a small rapidly disintegrating oral film form the area for absorption is optimized and the dissolution rate of the film is also optimized. The rapid onset of melatonin and valerian extract action from the delivery system provided by the subject invention can provide for rapid drug absorption, resulting in drug plasma pharmacokenetics more similar to an intravenous injection, with none of the vicissitudes associated with gastrointestinal (GI) administration, e.g., poor absorption, erratic absorption, first pass metabolism, food and dietary supplements effects on oral bioavailability.

A compound for use in inducing sleep having one or more of melatonin and valerian each in a cyclodextrin compound. A liposomal construct encapsulating the cyvlodextrin complex(es) through use of a hydrated or previously hydrated phospholipid. Also present in embodiments of the disclosed technology is an absorption enhancer and a solvent for the absorption enhancer.

A weight of the melatonin is between 0.05 milligrams and 5 milligrams, inclusive in some embodiments of the technology while a weight of the valerian is between 0.5 milligrams and 25 milligrams, inclusive in some embodiments of the disclosed technology. The compound is then produced into a water soluable strip in embodiments.

The absorption enhancer can be piperin and the solvent can be or include olive oil which carries the piperin. The compound further comprises a plasticizer in embodiments of the disclosed technology. The compound can further have within it one, two or more of myrcene, linalool, betacaryophyllene, gamma amino butyric acid, tryptophan or a derivative thereof, magnesium salts, chelates and/or a sedative.

The compound is designed to be (defined as "created for the purpose of", "given with instructions to", or "is used as such") be placed sub-lingually or buccally. The compound can be in a dissolvable rectangular strip of material and/or in a gum, lozenge, mint, tablet, or powder. The compound is absorbable through the mucosa which includes absorption of the melatonin and/or velarian through the mucosa.

The dissolving can result in a metabolic effect within 20, 10, 5, or minutes (based on testing performed) and can have a secondary metabolic effect within an hour.

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

DETAILED DESCRIPTION OF EMBODIMENTS OF THE DISCLOSED TECHNOLOGY

The present technology provides a pharmaceutical composition for sublingual or buccal administration of a hormone, namely on or both of melatonin and valerian. The hormones have relatively low to poor solubility in water or other aqueous solutions. The composition comprises the hormones which are, in a first step (in some embodiments), complexed with a beta cyclodextrin or another complexation agent and in second step (in some embodiments), encased in a liposome. In a third step (in some embodiments), the molecules encased in the liposome are then dehydrated. In a fourth step, the liposomal complex is then compounded into any of a number of dosage forms either a dissolvable strip of material, a gum (malleable solid which is designed to be chewed and at least partially dissolve during chewing), lozenge (hard and non-malleable solid which is designed to be chewed or sucked and dissolve), mint (hard and flavored with menthol), tablet (hard and unflavored; designed dissolve in the mouth), or powder forms for subingual, buccal, rectal, vaginal or even nasal application.

Uniquely and unexpectedly discovered during testing, the composition described above elicits a first effect denoting a preliminary Tmax (first peak of metabolic effect or maximum concentration) at around 5 to 10 minutes (where "around" is defined as "within one minute thereof") with a pronounced secondary effect within one hour denoting a secondary uptake at the level of the small intestine and a secondary and pronounced Tmax (second peak of metabolic effect or maximum concentration).

For purposes of the subject invention, it should be understood that the term "melatonin" is a specific hormone having low to poor water solubility. Melatonin is used as the active ingredient in compositions of the invention. It would also be understood that use of the term melatonin refers to other hormone active ingredients having low to poor water solubility, such as estrogens, progesterone, testosterone, and dihydrotestosterone. Accordingly, embodiments of the subject invention include compositions wherein an estrogen, progesterone, testosterone, or dihydrotestosterone, or combinations thereof, are substituted for or used with melatonin. It would also be understood that these hormones may be in their respective derivative form. Therefore, reference to melatonin, estrogens, progesterone, testosterone, or dihydrotestosterone includes any salt, prodrug, metabolite, isomer, or derivative thereof having low to poor water or aqueous solubility. "Low to poor water or aqueous solubility" is defined as having a solubility of greater than 10, 30, or 100 mass parts of water required to dissolve 1 mase part of the solute.

For purposes of the invention the term valerian extract refers to either an aqueous or ethanolic extract of the plant valeriana officinialis quantified to a specific quantity of valerenic acid. In accordance with certain embodiments of the present invention, the composition comprises a mixture of both melatonin and valerian extract complexed with beta cyclodextrin and subsequently encased in the core of a liposome. In certain embodiments, the liposomal complex can be administered as a powder, a tablet, a gum, a lozenge, a strip, a mint, a vaginal suppository, or an anal suppository.

The concentration of active ingredients, such as melatonin and/or valerian (alone or in combination), in the delivery form is, in some embodiments, in a range of about 2.5% to about 40%, and in some more specific embodiments, between about 10% to 20% (where "about" is defined as within/less than 1% thereof).

The pharmaceutical composition of the subject invention may further comprise other active molecules such as terpenes having as their main effect either a soporific or relaxant effect upon the central nervous system of the patient. Such terpenes for example can be, but are not limited to, myrcene or alpha linalool. These terpenes can also be complexed with beta cyclodextrin for enhanced solubility and bioavailability of the respective terpenes. Furthermore these complexed terpenes can be further encased into the liposomal complex protecting their stability and allowing for both enhanced sublingual absorption and enhanced absorption of the complex in the small intestine.

In embodiments of the disclosed technology, the composition of the subject invention is provided in a unit dose form such as dosed in a compressed tablet, strip, or gum for buccal or sublingual administration porviding rapid administration of the API upon sublingual or buccal administration of the composition.

The composition of the subject invention advantageously provides the active ingredient, e.g., a hormone such as melatonin having relatively low to poor solubility in aqueous solvents, in a liposomal complexed form. Being in a highly water soluble form, the melatonin can be directly absorbed into the bloodstream through the oral mucosa having been dissolved by the aqueous environment provided by saliva in the mouth or in the gastrointestinal tract. A further advantage of the drug delivery system of the subject invention includes enhanced and rapid oral mucosal absorption of the active provided in the composition. Accordingly, this drug delivery system provides for rapid onset of drug action with higher and more consistent bioavailability both with the initial onset between 5 and 10 minutes and the secondary absorption at the small intestine providing enhanced intestinal absorption and prolonged effect. The technology described herein can be used to treat insomnia, jet lag, and/or sleep related disorders.

The melatonin/valerian extract sublingual forms, in embodiments of the disclosed technology, range from approximately 0.1 mg (milligrams) to 100 mg total weight depending on the dosage form. In vitro dissolution from these rapid release formulations is substantially complete within 5 minutes and the form disintegrates under the tongue typically within a few minutes, such as less than 5 minutes, and in some cases, within one to three minutes, and in some cases, even within 30 seconds to about two minutes.

A secondary absorption of some of the complexed forms occurs at the level of the small intestine prolonging the effect of the formulation beyond that absorbed at the primary mucosal surface, thus prolonging the effect on duration of sleep and sleep intensity.

A single dose of active ingredient, e.g., melatonin, in some embodiments of the disclosed technology is between 0.01 mg to 3 mg and, in some more specific embodiments, between 0.2 and 2.0 mg. Valerian extract in such embodiments can be between 0.5 mg and 15 mg or more specifically between 1 mg and 10 mgs. When used in such low doses, compositions in accordance with the administration have a metabolic effect of at lest one hour and are effective in treatment of insomnia, or in causing extreme drowsiness or sleep in humans. Thus, the present invention can advantageously provide consistent and sufficiently high peak melatonin and valerenic acid blood plasma concentration (Cmax.). Consistently effective melatonin and valerenic acid blood plasma concentrations are thus achieved even when using lower melatonin and valerian extract doses than administered in currently available products.

The composition can also include various other compounds of lesser concentration, preferably from 0.01 to 0.1 mg per dose, such as linalool or myrcene by way of example.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described herein-above are also contemplated and within the scope of the disclosed technology.

I claim:

1. A compound for use in inducing sleep, comprising:
   melatonin in a cyclodextrin compound;
   valerian extract in a cyclodextrine compound;
   a liposomal construct encapsulating the cyclodextrine complexes through use of a hydrated phospholipid;
   an absorption enhancer;
   a solvent for said absorption enhancer.

2. The compound of claim 1, wherein a weight of said melatonin is between 0.05 milligrams and 5 milligrams, inclusive.

3. The compound of claim 2, wherein a weight of said valerian is between 0.5 milligrams and 25 milligrams, inclusive.

4. The compound of claim 3, wherein said compound is produced into a water soluble strip.

5. The compound of claim 1, wherein said absorption enhancer comprises piperin.

6. The compound of claim 5, wherein said solvent comprises olive oil as a solvent for said piperin.

7. The compound of claim 6, wherein said compound further comprises a plasticizer.

8. The compound of claim 1 further comprising at least two of myrcene, linalool, betacaryophyllene, gamma amino butyric acid.

9. The compound of claim 1, further comprising at least two of tryptophan or a derivative thereof, magnesium salts, chelates, and a sedative.

10. The compound of claim 8, wherein said compound is designed to be placed sub-lingually or buccally.

11. The compound of claim 10, wherein said compound is in a dissolvable rectangular strip of material.

12. The compound of claim 1, wherein said compound is in a gum, lozenge, mint, tablet, or powder form.

* * * * *